United States Patent [19]

Greenler et al.

[11] Patent Number: 5,783,155
[45] Date of Patent: Jul. 21, 1998

[54] SHEET FLOW FLUID SAMPLING APPARATUS

[75] Inventors: Leland S. Greenler, Stoughton; Grant R. Emmel; Farshid Feyzi, both of Madison; David W. Owens, Verona, all of Wis.

[73] Assignee: Wisconsin Alumni Research Foundation, Madison, Wis.

[21] Appl. No.: 664,489

[22] Filed: Jun. 17, 1996

[51] Int. Cl.⁶ ........................................ B01L 3/00
[52] U.S. Cl. ........................ 422/102; 422/99; 422/100; 422/104; 137/392; 137/624.11; 137/624.12; 137/624.15
[58] Field of Search ............... 137/624.11, 624.12, 137/624.15, 392; 206/219; 422/102, 104, 100, 99; 436/180

[56] References Cited

U.S. PATENT DOCUMENTS

| | | | |
|---|---|---|---|
| 3,296,858 | 1/1967 | Doury et al. | 73/170 |
| 3,817,274 | 6/1974 | Anderson | 137/392 |
| 3,844,311 | 10/1974 | McSwain | 137/624.11 |
| 3,878,376 | 4/1975 | Sholes, Jr. et al. | 137/624.11 X |
| 3,922,564 | 11/1975 | Kachuk et al. | 137/392 X |
| 4,140,011 | 2/1979 | Krupa et al. | 73/171 |
| 4,148,334 | 4/1979 | Richards | 137/389 |
| 4,245,499 | 1/1981 | Nguyen et al. | 73/171 |
| 4,270,564 | 6/1981 | Blackburn et al. | 137/240 |
| 4,491,146 | 1/1985 | Sveds | 137/341 |
| 4,546,795 | 10/1985 | Okamoto et al. | 137/624.15 |
| 4,645,073 | 2/1987 | Homan | 206/219 |
| 4,811,221 | 3/1989 | Sturman et al. | 364/420 |
| 5,016,196 | 5/1991 | Nelson et al. | 364/550 |
| 5,105,974 | 4/1992 | Busching | 220/694 |
| 5,118,628 | 6/1992 | Krimpen et al. | 436/39 |
| 5,154,188 | 10/1992 | Ebert | 128/898 |
| 5,167,802 | 12/1992 | Sandstrom et al. | 210/134 |
| 5,205,311 | 4/1993 | Wilkins | 137/14 |
| 5,230,865 | 7/1993 | Hargett et al. | 422/102 |
| 5,353,728 | 10/1994 | Strange | 114/74 R |
| 5,464,038 | 11/1995 | Kruto | 137/486 |

*Primary Examiner*—Harold Y. Pyon
*Attorney, Agent, or Firm*—Quarles & Brady

[57] ABSTRACT

An apparatus periodically samples fluid flowing across a surface by providing a plate for mounting flush with the surface. The plate has an aperture extending there through and a tubular body extends from the around the aperture with a passage in communication with the aperture. A sample collection vessel is removably attached to the body to receive fluid passing through the aperture and the passage. A valve member closes the aperture and moves when driven by an electromechanical device. The electromechanical device operates the valve member to alternately open and close the aperture during a defined sampling time to acquire a plurality of samples of the fluid flowing across the surface.

9 Claims, 3 Drawing Sheets

SHEET FLOW FLUID SAMPLING APPARATUS

This invention was made with United States Government support awarded by USGS. The United States Government has certain rights in this invention.

BACKGROUND OF THE INVENTION

The present invention relates to devices which acquire samples of fluid, such as rain water, as the fluid flows across a surface, such as that of a parking lot.

For environmental monitoring, it is often desirable to acquire samples of rain water and other fluids that flow across the ground at a particular site. For example, governmental regulations may require acquisition of such samples on property where hazardous wastes are stored or where toxic chemicals are used. The samples then can be analyzed to determine whether there is leakage from the storage facilities.

Typically one would wish to sample fluids flowing across the surface of the ground throughout a prolonged period of time, such as during a rainstorm. However, if an open vessel merely is placed into the ground, that container would quickly fill with fluid and thus, not acquire samples throughout the desired interval of time. Further, a continuously open vessel would become contaminated with debris that is not associated with the water sample and thus the fluid samples would not accurately reflect the character of the water flowing across the ground.

As a consequence it is desirable to provide an apparatus that can respond to the presence of fluid flowing across the surface of the ground, such as a parking lot, building site, road or walkway, automatically acquire samples of the fluid over a relatively long period of time and provide immunity to external contaminants.

SUMMARY OF THE INVENTION

A general object of the present invention is to provide an apparatus that samples fluid which flows across a surface. For example, the apparatus may acquire samples of rain water flowing across a parking lot, sidewalk, spillway or other surface on the ground for subsequent analysis to detect hazardous substances in the water flow.

Another object of the present invention is to provide that type of sampling apparatus which periodically acquires small samples of the fluid over a prolonged interval of time.

Yet another object of the present invention is to provide such a sampling apparatus which will be activated automatically by the presence of water flowing across the surface. By limiting activation of the device only in the presence of fluid flow, a battery powered device can be utilized in an efficient manner.

A further object of the present invention is to provide a sampling apparatus in which the user is able to define the length of time that the device is to be operated to periodically acquire samples, the length of time that each sample is acquired and how often the samples are acquired.

These objectives and others are fulfilled by an apparatus that has a body which mounts in the surface across which that fluid to be sampled flows. The body has opposing first and second surfaces with an aperture extending therebetween. The first surface is placed flush with the fluid flow surface and a vessel is placed adjacent to the second surface of the body to receive fluid passing through the aperture.

A valve member and a valve member operating mechanism are included to alternately open and close the aperture to permit fluid to enter the vessel. In the preferred embodiment of the sampling apparatus the valve member operating mechanism comprises an electromechanical device, such as a solenoid, connected to the valve member by a lever and a control circuit for driving the electromechanical device. The control circuit may include a sensor which detects when fluid is flowing across the surface and then activate a procedure timer which determines the duration of time during which samples of the fluid flowing across surface will be acquired. A valve timer determines how often and for how long an interval the valve member is to be opened. Another sensor may be provided to disable the apparatus after a given amount of fluid has been acquired in the vessel.

DETAILED DESCRIPTION OF THE INVENTION

Figure 1:
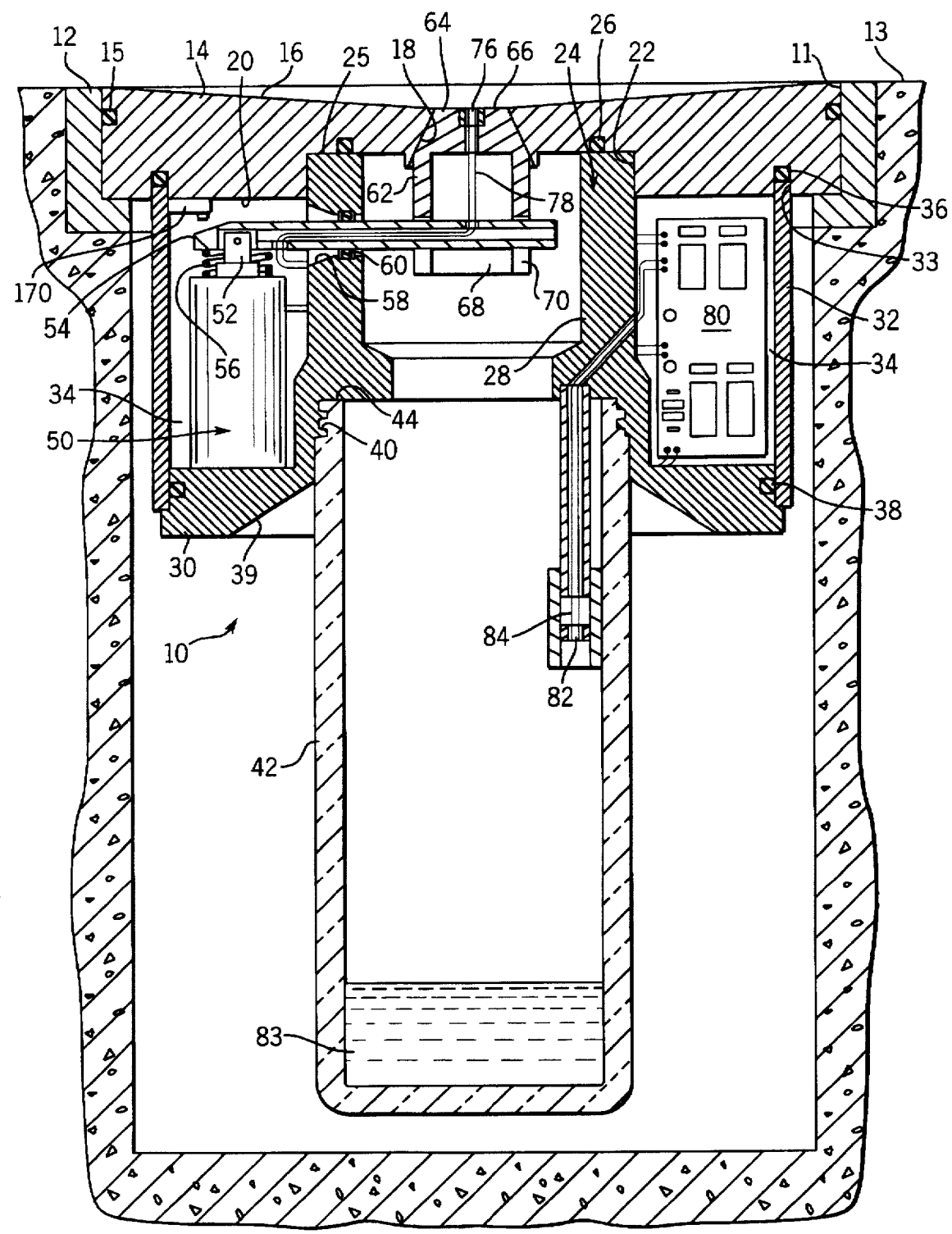
FIG. 1 is a cross sectional view of sheet flow water sampling apparatus according to the present invention.

With initial reference to FIG. 1, a fluid sheet flow sampling apparatus 10 includes an annular mount 12 that is firmly buried in the surface 13 across which flows the fluid to be sampled. For example, the surface 13 may be that of a parking lot, sidewalk or spillway at a facility where hazardous waste or toxic chemicals are stored. Thus, it is desirable periodically to sample rain water flowing across the surface 13 to determine whether it contains any hazardous waste or toxic chemicals. Annular mount 12 is located flush with the surface 13 so as not to impede the flow of water or other fluids. Alternatively, the annular mount may form the opening of a box that is buried in the ground to house the sampling equipment. Preferably the annular mount 12 has a circular central opening 11 in which a circular plate 14 is removably located. The outer periphery of the circular plate 14 has an annular groove that contains an O-ring 15 which provides a fluid-tight seal between the circular plate 14 and the annular mount 12. The exterior surface 16 of the circular plate 14 is concave with a circular aperture 18 extending between the lowest part of the exterior surface 16 and an opposing inner surface 20 of the plate. The circular aperture 18 is tapered and thus has a smaller opening in the exterior surface 16 than in the inner surface 20.

A recess 22 is formed centrally in the inner surface 20 of circular plate 14 surrounding the circular aperture 18. A tubular first housing 24 has one end 25 which tightly fits within the recess 22. Another O-ring 26 is located between the circular plate 14 and the first housing 24 to provide a water tight seal. The first housing 24 has a central passage 28 extending between end 25 which is received within recess 22 and an opposite end which has an outwardly projecting flange 30. A tubular second housing 32 extends around the first housing 24 between the outer perimeter of the flange 30 and a notch 33 in the inner surface 20 of plate 14, thus forming a housing chamber 34. A pair of O-rings 36 and 38 seal the second housing to the circular plate 14 and the first housing respectively.

Central passage 28 in the first tubular housing 24 has an opening 39 through the flange 30 with internal threads 40. A sample collection vessel, such as a glass jar, has a threaded open end 44 which is received within the opening 39 in the flange 30 and engages the internal threads 40 to secure the sample collection vessel 42 to the first housing 24.

A DC solenoid 50 is located within the housing chamber 34 and has a plunger 52 which can be selectively extended from or retracted into the solenoid body depending upon the polarity of a DC voltage applied to a coil inside the solenoid. Preferably the solenoid 50 is of a latching type so that a brief DC pulse can produce the retraction or extension of the plunger, thereby conserving power as compared to electromechanical devices which require the continuous application of electricity in order to maintain the plunger in either an extended or retracted state. The exposed end of the plunger 52 is pivotally connected to a valve lever 54. A compression spring 56 is positioned between the body of solenoid 50 and the valve lever 54 to bias the valve lever away from the body of the solenoid and provide additional force to extend the plunger 52 from the solenoid. The valve lever 54 extends through a hole 58 in the side of the tubular first housing 24 with an O-ring 60 providing a water tight seal between that housing and lever. The O-ring 60 also functions as a fulcrum about which the valve lever 54 pivots when acted upon the solenoid plunger 52.

The remote end of the valve lever 54 from solenoid 50 is connected to a valve member 62 which serves as a plug for the circular aperture 18 in the circular plate 14. The valve member 62 has a first end portion 64 which tapers to a small end surface 66. The angle of the taper corresponds to the taper of the circular aperture 18 so that the valve member 62 can close the aperture when positioned as shown in FIG. 1. The opposite end portion 68 of the valve member 62 is hollow and has a notch 70 there across. The valve lever 54 extends through the notch 70 to raise and lower valve member 62 within circular aperture 18 as the lever is acted upon by the solenoid 50, as will be described.

A pair of fluid flow sensing electrodes 76 are mounted spaced apart on the exposed end surface 66 of the valve member 62. The fluid flow sensing electrodes 76 are connected by a pair of wires 78 to a control circuit 80 located within the housing chamber 34 between the first and second housings 24 and 32, respectively. A pair of fluid level sensing electrodes 82 are positioned within the sample collection vessel 42 to detect when the level of fluid 83 therein reaches a given level. The fluid level sensing electrodes 82 is connected by wires 84 to the control circuit 80.

Figure 2:
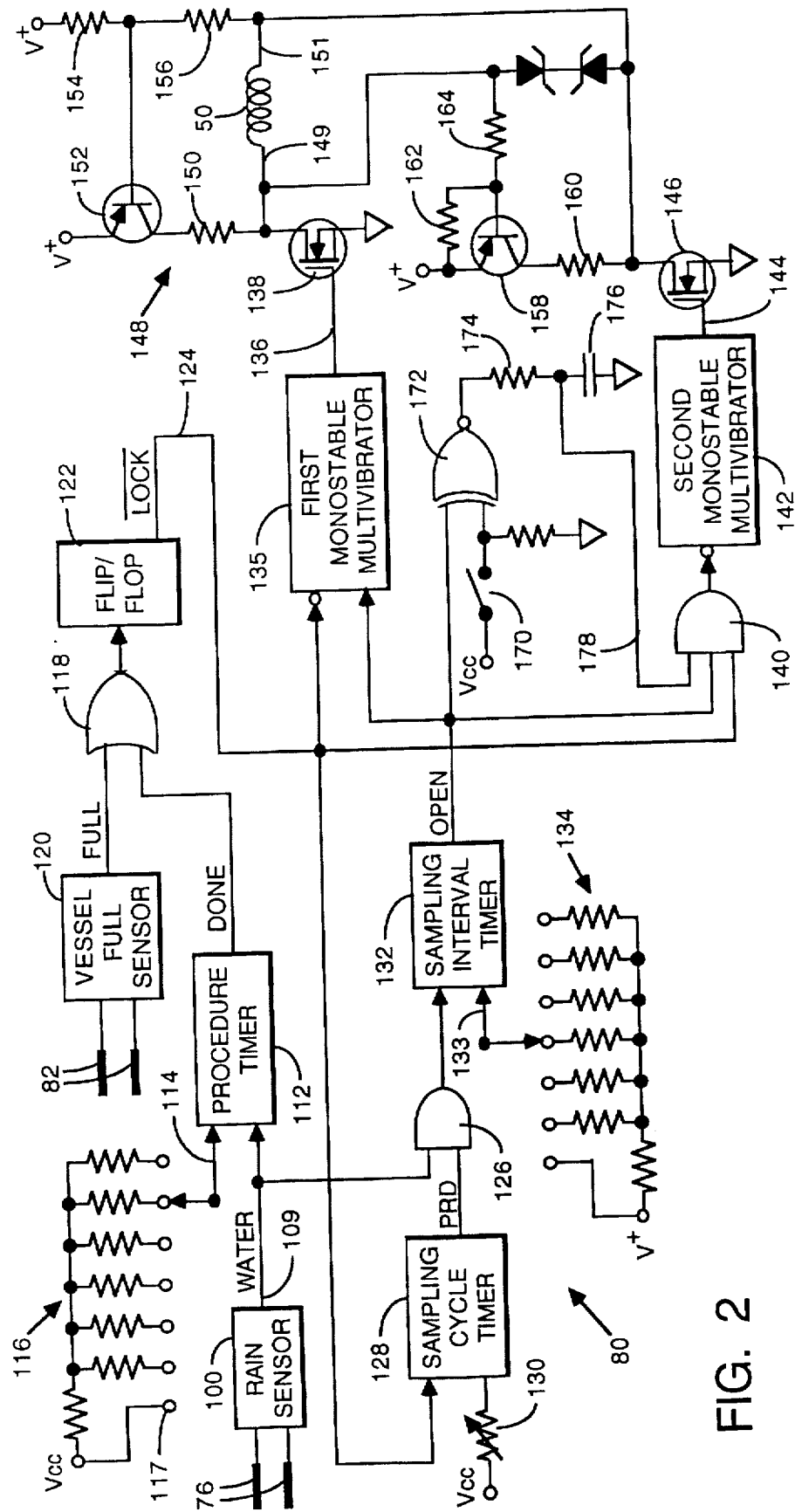
FIG. 2 is a schematic block diagram of an electronic circuit that controls the water sampling.

The operation of the fluid sheet flow sampling apparatus 10 is governed by the control circuit 80, which is illustrated schematically in FIG. 2. Fluid flow sensing electrodes 76 are connected to a rain sensor circuit 100 shown in detail in FIG. 3. The rain sensor circuit 100 comprises an oscillator 102 which produces a triangular wave on line 104 that is capacitively coupled to node 106 in order to minimize electroplating of the fluid flow sensing electrodes 76. One of the fluid flow sensing electrodes 76 is connected to circuit ground, while the other electrode is connected directly to node 106. The voltage level at node 106 is sensed by an inverting Schmidt trigger 108. As long as an open circuit exists between the fluid flow sensing electrodes 76, the output of the rain sensor circuit 100 at terminal 109 will be at a low logic level. However, when rain water or another electrically conductive fluid contacts both of the fluid flow sensing electrodes 76, the conductive path formed between the electrodes causes the output of the rain sensor circuit 100 to go to a high logic level. The output signal produced by the rain sensor circuit 100 is designated WATER.

Returning again to FIG. 2, the WATER output signal from the rain sensor circuit 100 is connected to the enable input of a procedure timer 112. The procedure timer determines how long samples of the fluid flowing across surface 13 will be acquired periodically. That duration of the sampling procedure is user selectable by changing the connection of a timing input 114 to a selected resistor within a resistor matrix 116. Each resistor in matrix 116 has a different resistance. Typically, the duration of the procedure can be selected in increments between five minutes and one hour with another matrix terminal 117 connected directly to the positive voltage source Vcc in order to define a procedure time of infinite duration. During the sampling operation, the procedure timer 112 produces a low level signal, designated DONE, at its output. The DONE signal is connected to one input of a dual input OR gate 118.

Figure 3:
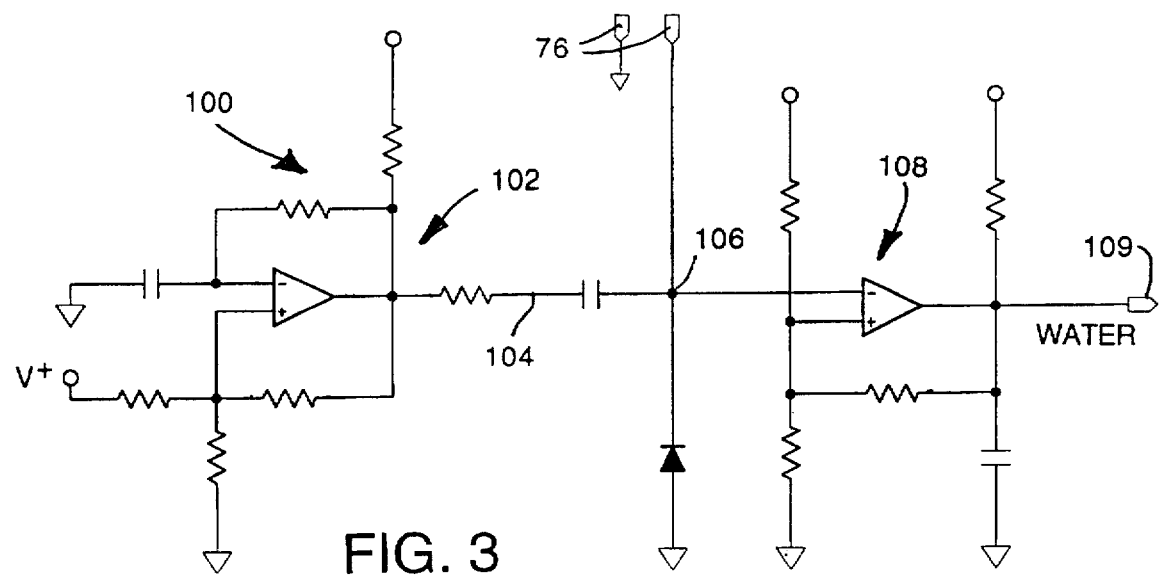
FIG. 3 is a detailed schematic diagram of water sensing circuits that are part of the circuit in FIG. 2.

The other input of OR gate 118 is connected to the output of a vessel full sensor circuit 120, which is identical to the rain sensor circuit 100 shown in FIG. 3, except that the vessel full sensor is connected to the fluid level sensing electrodes 82 within the sample collection vessel 42. When the fluid within the sample collection vessel 42 reaches the fluid level sensing electrodes 82, a conductive path is established between the electrodes and the vessel full sensor circuit 112 produces a high logic level signal, designated FULL, at its output.

The output of OR gate 118 is connected to the toggle input of a flip-flop 122. The flip-flop produces an output signal designated $\overline{LOCK}$ which when true (a low logic level) terminates any sampling procedure that is in progress, as will be described.

The $\overline{LOCK}$ signal is supplied to an enable terminal of the sampling cycle timer 128 to continuously produce a pulsed signal PRD during the sampling procedure. The sampling cycle timer 128 generates high level signal pulses at intervals which define the sampling cycle, i.e. the interval between the PRD signal pulses is equal to the interval between times that valve member 62 is to open circular aperture 18 and allow fluid to enter the sample collection vessel 42. For example, every 60 seconds the sampling cycle timer 28 produces a 50 millisecond pulse of the PRD signal. That sampling cycle interval is determined by the user setting a potentiometer 130. Alternatively, the potentiometer 130 could be replaced by a resistor matrix similar to 116 used with the procedure timer 112. A fixed resistor also could be employed in place of potentiometer 130 to set the sampling cycle interval at a single length of time.

The true WATER signal (a high logic level) from rain sensor circuit 100 gates the PRD signal pulses through AND gate 126 to the trigger input of a sampling interval timer 132. The sampling interval timer 132 produces a high logic level at its output for a user selectable time interval after receipt of a high trigger pulse from AND gate 126. The duration of the high level output from sampling interval timer 132 is determined by a user selectable connection of a timing input 133 to different valued resistors in matrix 134. The connection to resistor matrix 134 allows the sampling interval, which is the period of time that the valve member 62 opens circular aperture 18 to allow water to enter the sample collection vessel 42, to be varied in different increments between one and thirty seconds, for example. In addition, the timing input of the sampling interval timer may be connected directly to the positive voltage $V^{cc}$ to continuously open the circular aperture 18 once the sampling interval timer has been triggered. Alternatively, a single fixed resistor or potentiometer may be used in place of the resistor matrix 134.

With continuing reference to FIG. 2, the output of the sampling interval timer 132 produces a signal designated OPEN which is connected to a solenoid driver section of the control circuit 80. Specifically, the OPEN signal is applied to the trigger input of a first monostable multivibrator 135. The first monostable multivibrator 135 is triggered by the rising edge of the OPEN signal and responds by producing a brief output pulse on line 136 which is connected to the gate electrode of a first field effect transistor 138. The output of the sampling interval timer 132 also is connected via a three-input AND gate 140 to the trigger input of a second monostable multivibrator 142. When the second monostable multivibrator is triggered a brief pulse is produced on output line 144 that is connected to the gate electrode of a second field effect transistor 146. Another input of AND gate 140 is connected to the output of flip-flop 122 to receive the LOCK signal.

Field effect transistors 138 and 146 form part of a conventional H-bridge 148 which supplies direct current to the solenoid 50. Specifically, the source-drain conduction path of the first field effect transistor 138 is connected between a first terminal 149 of the solenoid 50 and circuit ground. The first terminal 149 is connected to the positive voltage supply V$^+$ by a series of connection of resistor 150 and the emitter-collector conduction path of bipolar transistor 152. The base of bipolar transistor 152 is coupled to the positive voltage source V$^+$ by resistor 154. A second terminal 151 of solenoid 150 is coupled to the base of bipolar transistor 152 by resistor 156 and to circuit ground by the source-drain conduction path of the second field effect transistor 146. A second bipolar transistor 158 has its emitter-collector conduction path connected in series with resistor 160 between the positive voltage supply V$^+$ and the second terminal 151 of the solenoid 150. Resistors 162 and 164 are connected to bias the base of second bipolar transistor 158.

As will be described in detail, when the first monostable multivibrator 135 produces an output pulse on line 136, the H-bridge 148 is activated to apply direct current through the solenoid 150 in a direction which extends the plunger 52 of the solenoid 50, thereby operating the valve lever 54 in FIG. 1 to move the valve member 62 away from contact with the circular plate 14 and opening circular aperture 18. Because the solenoid 50 is a latching type, the plunger remains in the extended position after the pulse from the first monostable multivibrator 135 terminates. When it is time to close the circular aperture 18, second monostable multivibrator 142 emits a pulse on line 144 which activates the H-bridge 148 to apply the opposite polarity direct current to the solenoid 50 which causes a retraction of the plunger 52 and closure of circular aperture 18. Because the solenoid 50 is a latching type, the aperture will remain closed after termination of the pulse from the second monostable multivibrator 142.

When power is initially applied to the control circuit 80 from a battery (not shown), a conventional power-on-reset circuit (not shown) causes the various timers and logic elements to assume a predefined state for initiating operation of the sampling control. When rain water or another conductive fluid flows across surface 13 in the vicinity of the sheet flow fluid sampling apparatus 10, the fluid will enter the depression formed by the concave exterior surface 16 of plate 14 shown in FIG. 1. The fluid will cover the exposed ends of the two fluid flow sensing electrodes 76 producing a conductive path there between. This electrical coupling between the fluid flow sensing electrodes 76 triggers the rain sensor circuit 100 in FIG. 2, producing a true WATER signal. When this occurs, the procedure timer 112 is activated and begins timing the sampling procedure period for the apparatus 10. The true WATER signal also causes the AND gate 126 to convey pulses from the sampling cycle timer 128 to the trigger input of the sampling interval timer 132. This activation begins producing high level pulses of the OPEN signal at the output of the sampling interval timer 132. These high level pulses of the OPEN signal have a duration determined by the setting of resistor matrix 134 and occur at periods determined by the setting of the potentiometer 130 connected to the sampling cycle timer 128.

The rising edge of each pulse of the OPEN signal triggers the first monostable multivibrator 135 generating a brief (e.g., 50 ms) high logic level pulse on output line 136. As previously described, such a pulse activates the H-bridge 148 to apply a DC current through solenoid 50 along with force from spring 56 which causes an extension of plunger 52 (see FIG. 1). This action pivots the valve lever 54 about O-ring 60, retracting the valve member 62 into the first housing 24 and away from the walls of aperture 18. That aperture 18 opens allowing water flowing across surface 13 into exterior surface 16 continues to flow downward through passage 28 into the sample collection vessel 42. The valve member 62 is held in the open position by the latching mechanism of solenoid 50.

At the end of the sampling interval, the falling edge of the OPEN signal triggers the second monostable multivibrator 142 thereby emitting a brief (e.g. 50 ms) high logic level pulse on output line 144. This pulse activates the H-bridge 148 to apply direct current in the opposite direction through the solenoid 50 that produces an electromagnetic field which retracts the plunger 52. That retraction pivots valve lever 54 forcing the valve member 62 against the walls of circular aperture 18 in the circular plate 14. The tapered walls of circular aperture 18 and the first end portion 64 of valve member 62 provide a line seal interface which closes the aperture.

Circular aperture 18 remains closed until the sampling cycle timer 128 again emits a brief positive pulse of the PRD signal which causes the sampling interval timer 132 to produce high level OPEN signal pulse that results in another opening of the circular aperture 18.

This periodic opening and closing of circular aperture 18 continues as long as the following three conditions exist: (1) conductive fluid connects the fluid flow sensing electrodes 76, (2) fluid within the sample collection vessel 42 remains below the fluid level sensing electrodes 82, and (3) the procedure timer 112 produces a false DONE signal. If water or another conductive fluid no longer provides a conductive path between fluid flow sensing electrodes 76, the rain sensor circuit 100 in FIG. 2 will cease to emit a true WATER signal and disables the procedure timer 112. This action does not reset the procedure timer which will resume timing the sampling procedure where it was interrupted should fluid again provide a conductive path between fluid flow sensing electrodes 76. Thus, a false DONE signal still is produced by the procedure timer at the end of the set time. The false WATER signal that is applied to an input of AND gate 126 also prevents pulses of the PRD signal from triggering the sample interval timer 132 and in turn the production of the periodic active OPEN signal. Thus, solenoid 50 will not be energized and the valve member 62 will remain in the closed state until the WATER signal again goes true.

In the second event, when the conductive fluid in the sample collection vessel 42 reaches the fluid level sensing electrodes 82, the vessel full sensor 120 produces a true FULL signal which toggles flip-flop 122 and generates a low level LOCK signal on line 124. This low level signal disables the first monostable multivibrator 135 and triggers the second monostable multivibrator 142 which energizes the H-bridge 148 and retracts the solenoid plunger 52, thereby closing the circular aperture 18 with the valve member 62. The low level $\overline{\text{LOCK}}$ signal on line 124 from flip-flop 122 also disables the sampling cycle timer 128 so that, even though rain water still may be connecting fluid flow sensing electrodes 76, the OPEN signal remains false causing the valve member 62 to stay closed.

In the third case, the lapse of procedure timer 112 produces a true (high logic level) DONE signal which toggles flip-flop 122 to produce an false $\overline{\text{LOCK}}$ signal on line 124. This low level signal as described previously causes the valve member 62 to close the circular aperture 18, if that aperture was previously open, and disables the sampling cycle timer 128. Thus, at the end of the sampling procedure, the valve member 62 will stay closed.

With reference to FIG. 1, an animal walking across the plate 14 or another object traveling across surface 13 may depress the valve member 62 downward into the first housing 24 thereby opening circular aperture 18 inadvertently. This downward pressure on the valve member 62 causes a mechanical pivoting of valve lever 54 which pulls the solenoid plunger 52 out of the body of the solenoid 50. Because the solenoid 50 preferably is a latching type, the valve member 62 will remain in the open position even though electricity is not being applied to the solenoid. If this inadvertent operation of the valve member 62 occurs in the absence of conductive fluid flowing across the sensing electrodes 76, the control circuit 80 will not otherwise operate to close the valve. Thus, the valve will stay open allowing debris and other contaminants to enter the sample collection vessel 42.

To prevent the circular aperture 18 from remaining open due to such inadvertent manual operation of valve member 62, a switch 170 is positioned within the device so as to be closed by the valve lever 54 in the open position. Referring to FIG. 2, closure of the valve member closed sensing switch 170 and applies a high logic level to one input of an exclusive NOR gate 172. Another input of exclusive NOR gate 172 receives the OPEN signal from the output of the sampling interval timer 132. Normally, when the OPEN signal is high, the valve member 62 and level 54 are in an open state thereby closing switch 170 so that both inputs of the exclusive NOR gate 172 will be at a high logic level. Similarly, when the OPEN signal is at a low level, the valve member 62 and lever 54 will be in a closed state which opens switch 170. Thus, both inputs of the exclusive NOR gate 172 normally should be at the same logic level causing the NOR gate to produce a high level output that is applied to the third input of AND gate 140. However, in practice one will realize that the OPEN signal changes states a short period of time before the mechanical action of the lever 54 produces a change in state of switch 170. As a consequence, the output of the exclusive NOR gate 172 is applied to an RC time delay circuit formed by resistor 174 and capacitor 176. Therefore, the two inputs of the exclusive NOR gate 172 must be at different logic levels for a given period of time before the voltage on line 178 goes low.

However, when an external force pushes the valve member 62 downward into the first housing 24, thereby opening the aperture 18 without energizing solenoid 50, switch 170 closes providing a high logic level at one input of the exclusive NOR gate 172 while the other input receives a low level OPEN signal. After the time delay provided by the RC circuit at the output of the exclusive NOR gate 172, the logic level on line 178 will go low which results in the trigger input of the second monostable multivibrator 142 going low. This produces a brief high level output pulse on line 144 that energizes the solenoid 50 to retract plunger 52 and close the circular aperture 18. Thus, sensing switch 170 and components 172–176 provide a mechanism which automatically closes the circular aperture 18 should an external force inadvertently move the valve member 62 into an open position.

We claim:

1. An apparatus for sampling fluid flowing across a surface, said apparatus comprising:

a plate for mounting in the surface, wherein the plate has opposed first and second surfaces with an aperture extending between the first and second surfaces;

a first housing extending from the second surface of said plate and having a passage in communication with the aperture, said first housing has a hole therethrough;

a vessel removably attached to said first housing to receive fluid passing through the aperture and the passage;

a valve member within said first housing for opening and closing the aperture to fluid flow;

a second housing extending around said first housing and creating a chamber; and a mechanism within said second housing for operating said valve member to intermittently open and close the aperture in said plate, said mechanism comprising a lever extending through the hole in the first housing and engaging said valve member, a solenoid in the chamber and connected to said lever to produce movement of said valve member to open and close the aperture in said plate, and a control circuit having a timer for energizing the solenoid.

2. The apparatus as recited in claim 1 further comprising a fulcrum located in the hole of the first housing and about which said lever pivots.

3. The apparatus as recited in claim 1 further comprising a sensor for detecting the presence of fluid flowing across the surface, wherein operation of said control circuit is responsive to said sensor.

4. The apparatus as recited in claim 1 further comprising a sensor for detecting a predefined level of fluid in said vessel, wherein operation of said control circuit is responsive to said sensor.

5. The apparatus as recited in claim 1 wherein the first surface of said plate is concave.

6. The apparatus as recited in claim 1 wherein the aperture in said plate is tapered and said valve member has a conically shaped portion.

7. The apparatus as recited in claim 1 wherein said first housing has a tubular portion with a first end abutting said plate, and a second end having an outwardly extending flange.

8. The apparatus as recited in claim 1 wherein said control circuit comprises:

a procedure timer which determines length of time during which said apparatus will periodically gather samples of the fluid flowing across the surface; and a valve timer which determines how often the aperture to be opened and a given interval of time that the aperture is to be in an open state.

9. The apparatus as recited in claim 8 wherein said valve timer comprises:

a sampling cycle timer which determines a sample period corresponding to am amount of time between when said solenoid is activated to open the aperture; and a sampling period timer that determines the given interval of time that the aperture is open.

* * * * *